United States Patent [19]

Harris

[11] Patent Number: 4,550,016
[45] Date of Patent: Oct. 29, 1985

[54] COMPOSITE CYTOLOGIC COUNTERSTAIN FORMULATION

[76] Inventor: Cynthia J. Harris, Burke, Va.

[21] Appl. No.: 429,662

[22] Filed: Sep. 30, 1982

[51] Int. Cl.⁴ .................. G01N 31/00; G01N 33/48
[52] U.S. Cl. ............................. 424/3; 424/7.1; 436/64
[58] Field of Search .............. 424/3, 7.1; 436/64

[56] References Cited

U.S. PATENT DOCUMENTS 3,440,317  4/1969  Martinez .................. 424/1.7

OTHER PUBLICATIONS

Clark (Ed.), *Staining Procedures*, 4th Ed. Williams and Wilkins, London 1981, pp. 208–209.
Lillie, R. D., *Histopathologic Technic and Practical Histochemistry*, 3rd Ed., McGraw-Hill, N.Y., 1965, pp. 561–565.

*Primary Examiner*—Christine M. Nucker
*Attorney, Agent, or Firm*—Diller, Ramik & Wight

[57] ABSTRACT

A composite cytologic counterstain formulation and the method of using it are disclosed, the composite counterstain being effective to allow a sequence of staining steps for cytologic specimens which, within a few minutes only, produces a stained specimen having optical contrast and coloration closely approximating that attained by the complex and time-consuming Papanicolaou method.

3 Claims, No Drawings

COMPOSITE CYTOLOGIC COUNTERSTAIN FORMULATION

BACKGROUND OF THE INVENTION

The classic method of preparing a cytologic smear specimen involves staining by the Papanicolaou method. This method is complex and time consuming. A properly prepared specimen according to this method will normally require over one hour to complete. The specimens so obtained exhibit excellent contrast and coloration under microscopic examination and are the standard by which diagnostic cytology is carried out. The use of so-called "modified" Papanicolaou stains allows this time to be reduced by about one-half.

However, the elapsed time between obtaining the cytologic smear and the production of the specimen suitably stained for cytologic diagnosis is a definite disadvantage, and it would be extremely useful in the diagnostic field if a method could be devised to permit rapid attainment of stained cytologic specimens whose contrast and coloration were sufficiently identical to that which is obtained by Papanicolaou staining as to allow proper diagnosis by the well-established criteria developed with such latter staining.

Aspiration biopsy of lesions in selected tissues and organs using a 22 or 23-gauge needle (thin-needle or fine-needle biopsy) has evolved into a useful and safe technique. Thyroid nodules, pancreatic tumors, lung nodules, breast masses and lymph nodes are most commonly biopsied, often resulting in a definitive diagnosis. The information gained from this technique is useful in staging neoplasms, directing further diagnostic studies, guiding therapy and rendering prognoses. In some instances, the procedure may obviate further diagnostic studies, resulting in less trauma to the patient and also a definite cost savings.

While thin-needle aspiration biopsy has gained in popularity and currently is in widespread use, its success is dependent upon the proper handling and preparation of the aspirated material.

Good cellular preservation is a prerequisite for satisfactory cellular display. The cytologist should be called upon to assist in this technique so as to assure proper fixation and handling of the aspirate. The accuracy with which these small samples of specimen are prepared plays a major role in assessing morpholigic differences between normal and abnormal cells.

Among the benefits of having the cytologist prepare and collect the aspirated specimen are:
1. Abnormal cells are more accurately interpreted.
2. Conclusive diagnosing becomes easier with cells that consistently exhibit abnormalities.
3. Cytomorphology from different observers will agree more closely.
4. Time is saved screening a satisfactory cellular slide.
5. Progress in new areas of cytology will not be underestimated by an unsatisfactory reproduction of the specimen on a slide.

Although aspiration biopsy of pulmonary lesions was first described by Menetrier in 1886, acceptance and popularization of the technique awaited recent technological advances including image intensification and biplanar telefluoroscopy as well as improvements in needle design and the application of CAT scan to the procedure. Most of the modern pioneering work in fine needle aspiration cytology has emanated from the Swedish experience, however, in the past few years we have seen a rapid awakening of interest in aspiration cytology, particularly pulmonary aspiration in this country with a concomitant increase in research and study.

In the proper setting and hands percutaneous lung aspiration is an economical, rapid, safe and accurate method for the diagnosis of pulmonary nodules. In the past, negative sputum and bronchoscopic studies (a rule rather than exception) have led routinely to an open procedure in the diagnosis of such lesions. Although large bore needle biopsies have been available, they have been generally avoided due to their relatively high rates of morbidity. The introduction of fine needle aspiration has added a new dimension to the interpretation of pulmonary masses: A technique combining low morbidity approaching that of bronchoscopy and diagnostic accuracy approaching that of open biopsy. In addition, it is a procedure employing only topical anesthesia which can be performed on an outpatient basis.

Although the clinical pulmonary literature has traditionally referred to bronchoscopy as they key closed chest diagnostic technique, there is growing appreciation of the advantages of fine needle aspiration over this procedure in not only peripheral but also in centrally located lesions. Although the morbidity is slightly higher in aspiration, it is invariably of a minor and transitory nature. In general aspiration is tolerated much better by the patient than bronchoscopy, causing little or no discomfort. Consquently, there is increasing appreciation for and confidence in the procedure and it is often used in increasing proportions of cases in lieu of bronchoscopy in the interpretation of pulmonary nodules. One of the arguments often heard against transthoracic lung aspiration is that it is of limited value since a malignant diagnosis most often necessitates a thoracotomy for diagnosis. Although these statements could be made with some justification for bronchoscopy, a fact which in no way limits the use of that technique, they are not applicable to fine needle aspiration. Not only does this diagnostic modality provide the surgeon with valuable preoperative information, but in many instances makes thoracotomy with its significant risks of morbidity and mortality unnecessary. Instances in which thoracotomy can often be negated are as follows:
1. A malignant diagnosis in a poor surgical risk patient or if a lesion is inoperable for cure.
2. The diagnosis of a pulmonary lesion as metastatic malignancy.
3. The diagnosis of small cell undifferentiated carcinoma.
4. A diagnosis negative for malignancy.

A special note is called for here on the term "negative" as applied to pulmonary aspiration. As opposed to other areas of cytology, "negative" in lung aspiration has very specific criteria and definitions, it does not simply mean the absence of malignant cells on a specimen but rather:
A. The physician performing the aspiration is convinced that the needle was in the lesion in question.
B. The cytologic preparation is adequate in fixation, staining, and cellularity.
C. No malignant cells are present.
D. The cytologic interpretation is consistent with the clinical and radiologic findings.

Only when a specimen meets these criteria should it be signed out as negative. In addition, negative aspirations are usually repeated at least once before the final report is issued. When used in this highly structured way a negative aspiration report can safely be used as the basis for following the patient radiologically at 3, 6 and 12 month intervals rather than intervening surgically. Using negative reports in this manner, the risk of morbidity and mortality due to false negative report is far less than that due to surgery.

In addition to the diagnosis of lung nodules, percutaneous lung aspiration also provides an excellent means of obtaining material for bacterial and fungal cultures as well as the rapid diagnosis of organisms such as *Pneumocytis carinii*.

BRIEF SUMMARY OF THE INVENTION

The invention is directed to the field of cytopathology and, more specifically, to an improved stain and method which allows much more rapid cytological diagnosis of human cells. Typically, a cell spread specimen may be prepared for microscopic examination within about three minutes and the cells may then be accurately diagnosed with respect to normal and abnormal behavior and functional differentiation to provide requisite diagnosis for various conditions including tumor type.

Basically, the technique of this invention involves the steps of fixing the specimen on the slide, staining the specimen in an alcoholic solution of hematoxylin, hydrating the specimen, staining the specimen in an alcohol-based composite counterstain, hydrating the specimen and then dehydrating, clearing and covering the specimen. The staining method typically consumes about three minutes time.

The composite counterstain allows the elimination of a time-consuming and complex series of staining, hydration and rinsing steps necessary for conventional Papanicolaou staining and is largely responsible for the rapidity with which specimens can be prepared with this invention. The composite nature of the counterstain is due not only to the presence therein of a plurality of stain or dye entities but also to the presence of the alcohol base and acids, these composite entities cooperatively producing a rapid and simultaneous uptake of the several stains without detrimental effect or interference among the separate and distinct die components.

DETAILED DESCRIPTION OF THE INVENTION

The preferred composite counterstain of this invention is formulated as follows:

| | |
|---|---|
| absolute methanol | 250 ml |
| 95% ethanol | 680 ml |
| glacial acetic acid | 20 ml |
| phosphotungstic acid | 4 gms. |
| aqueous solution (10% TDC) orange G | 6 ml |
| aqueous solution (3% TDC) light green SF yellowish | 20 ml |
| aqueous solution (20% TDC) eosin Y | 20 ml |

In the above composite counterstain, the abbreviation TDC means "total dye content". The stains specified are powders having a percent dye content certified by the Biological Stain Commission. Thus, to prepare the aqueous solution of orange G above, this dye was obtained as a powder certified to contain 80% dye and 12.5 grams of this powder was dissolved in distilled water up to 100 ml to provide the 10% TDC solution.

All stains as used herein should be certified by the Biological Stain Commission and by experimentation it was found that the above powdered certified dyes as obtained from Fisher Scientific Company of Pittsburgh, Pa. gave the best results.

The orange G is identified by registration number of the Chemical Abstract Service, CAS Reg. 1936-15-8 and is listed as Fisher catalog number 0-267, color index 16230. The light green SF yellowish, CAS Reg. 5140-20-8 is listed as Fisher catalog number 0-3382, color index 42095. The eosin Y, CAS Reg. 17372-87-1 is listed as Fisher catalog number E-510.

In the above preferred counterstain, the orange G is present in weight amount of 0.6 gms, the light green SF yellowish is present in weight amount of 0.6 grams and the eosin Y is present in weight amount of 4.0 grams, all per liter of the composite counterstain. However, these components may be present in the following ranges:

| | |
|---|---|
| orange G | 8–18% TDC (0.48–1.08 gm/liter) |
| light green SF yellowish | 2–8% TDC (0.4–1.6 gms/liter) |
| eosin Y | 10–25% TDC (2–5 gms/liter) |

The glacial acetic acid may be present in the range of about 10–30 ml/liter and the phosphotungstic acid may be present in the range of about 2–8 grams/liter.

The absolute methanol and the 95% ethanol components must be present in about the volumes specified above.

To prepare a specimen according to this invention, the following procedure is used, subsequent to application of the cell spread on a microscope slide followed by any accepted method of preserving and fixing the cytologic cell spread thereon (e.g., by use of 95% ethanol or of any commercial water soluble cytologic spray fixative):

| Bath | time |
|---|---|
| 1. tap water | 5–10 dips (until surface is smooth) |
| 2. Gill's hematoxylin II | 30 sec–1 min, including 10 dips initially |
| 3. tap water | 5 dips |
| 4. tap water | 10 sec |
| 5. composite counterstain | 30 sec including 10 dips initially |
| 6. tap water | 5 dips |
| 7. tap water | 5 dips |
| 8. absolute ethanol | 10 dips |
| 9. absolute ethanol | 10 dips |
| 10. xylene | 5 dips |
| 11. xylene | 5 dips, and then coverslip. |

The dips should be effected at the rate of about two per second. Thus, the above method, involving only eleven baths, will ordinarily require only about three minutes for preparation of the specimen for microscopic examination and diagnosis.

The Gill hematoxylin II listed above is the preferred stain for step 2 and is available from Fisher Scientific Company.

Although the composition and method of this invention were developed primarily for use in laboratory screening of fine needle aspirated specimens where rapidity of diagnosis is the principal objective, they are also usable in conjunction with various fluid specimens, Pap smears, skin scrapings, wound touch preps, or any other cytologic cell spreads which are microscopically examined and interpreted on the basis of the known criteria and standards set by the profession.

Although the above specified stains as used in the composite counterstain are those which are preferred because they have given the best results and are well known certified stains, it will be appreciated that any acceptable equivalents may be used so long as the concepts of this invention are not violated. That is, the stained specimen must in any event possess contrast and coloration at least closely approximating those characteristics obtained by conventional Papanicolaou staining and the procedure described above must be attainable, i.e., the procedure must be such that the properly stained specimen is obtained within a few minutes and this, in turn, requires a minimum of baths as above noted and the rapidity of dye uptake inherent in the composite counterstain as specified.

What is claimed is:

1. A method of rapid cytological diagnosis of human cells comprising the steps of
    (a) fixing a specimen on a slide,
    (b) staining the specimen in a solution of hematoxylin,
    (c) hydrating the specimen, and thereafter,
    (d) staining the specimen in a composite cytologic counterstain for obtaining within a few minutes a specimen which when examined by a microscope provides a visual image exhibiting contrast and coloration comparable to that obtained by Papanicolaou method of staining, which consists essentially of 6 ml of an aqueous solution of about 8–18% total dye content of orange G, 20 ml of an aqueous solution of about 2–8% total dye content of light green SF yellowish, 20 ml of an aqueous solution of about 10–25% total dye content of eosin Y, from 20–30 ml of glacial acetic acid, from 2–8 grams of phosphotungstic acid, and the balance, to make one liter, of a mixture of methyl and ethyl alcohols.

2. The method as defined in claim 1 wherein the methyl alcohol is absolute and is present in the amount of 2.50 ml and the ethyl alcohol is 95% ethyl alcohol present in amount of 680 ml.

3. The method as defined in claim 1 wherein the aqueous orange G is present as a 10% total dye content aqueous solution, the light green SF yellowish is present as a 3% total dye content aqueous solution; and the eosin Y is present as a 20% total dye content aqueous solution.

* * * * *